(12) United States Patent
Risch et al.

(10) Patent No.: US 7,227,047 B2
(45) Date of Patent: Jun. 5, 2007

(54) BUTADIENE AND ISOBUTYLENE REMOVAL FROM OLEFINIC STREAMS

(75) Inventors: Michael A Risch, Seabrook, TX (US); John Di-Yi Ou, Houston, TX (US); Cor F. Van Egmond, Pasadena, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 450 days.

(21) Appl. No.: 10/646,142

(22) Filed: Aug. 22, 2003

(65) Prior Publication Data

US 2005/0043575 A1 Feb. 24, 2005

(51) Int. Cl.
*C07C 5/05* (2006.01)
*C07C 5/08* (2006.01)

(52) U.S. Cl. .................. 585/329; 585/259; 585/251
(58) Field of Classification Search ............... 585/329, 585/259, 251
See application file for complete search history.

(56) References Cited

U.S. PATENT DOCUMENTS

| | | | |
|---|---|---|---|
| 4,454,367 A | 6/1984 | Sakurada et al. ........... 585/533 |
| 4,645,576 A | 2/1987 | Takezono et al. ............. 203/30 |
| 5,227,553 A | 7/1993 | Polanek et al. ............. 585/259 |
| 5,955,640 A | 9/1999 | Paludetto et al. ........... 585/314 |
| 6,169,218 B1 | 1/2001 | Hearn et al. ................. 585/260 |
| 6,215,036 B1 | 4/2001 | Dorbon et al. ............. 585/664 |
| 6,242,662 B1 * | 6/2001 | Dorbon et al. ............. 585/670 |
| 6,433,242 B1 * | 8/2002 | Wiese ........................ 585/800 |
| 2002/0002316 A1 | 1/2002 | Girolamo et al. ........... 585/510 |
| 2002/0128528 A1 | 9/2002 | Pinault et al. .............. 585/259 |
| 2003/0100811 A1 | 5/2003 | Dakka et al. ............... 585/510 |
| 2004/0010171 A1* | 1/2004 | Marchionna et al. ........ 585/332 |

FOREIGN PATENT DOCUMENTS

WO WO 01/46095 6/2001

OTHER PUBLICATIONS

Adham, Kamal. "Classify Particles Using Fluidized Beds," www.cepmagazine.org, pp. 54-57, (Sep. 2001).

* cited by examiner

*Primary Examiner*—Thuan Dinh Dang

(57) ABSTRACT

A process is disclosed for selectively removing isobutene and butadiene from a stream, the process comprising contacting the stream with a hydrogenation catalyst to hydrogenate butadiene and an oligomerization catalyst to oligomerize isobutene.

12 Claims, 1 Drawing Sheet

BUTADIENE AND ISOBUTYLENE REMOVAL FROM OLEFINIC STREAMS

FIELD

This invention relates to a process for removing butadiene and isobutylene from olefinic streams, particularly $C_4$ olefinic streams.

BACKGROUND

Linear butenes (1-C4= and/or 2-C4=) are important feedstocks in a number of commercial processes. However, such feedstocks are often also required to contain low levels of both butadiene and isobutylene (iC4=) impurities. For example, 1-butene (1-C4=) can be used in the production of linear low density polyethylene (LLDPE), but the feedstock must contain less than 50 ppm of butadiene and less than 0.3~1.0 wt % isobutylene. Similarly, linear butenes can be oligomerized to produce near linear alpha olefins (NLAOs) useful in the production of surfactants, but again there are severe restraints on the levels of butadiene and isobutylene in the feedstock.

A variety of processes are available for producing C4 olefinic streams including, for example, steam cracking, fluid catalytic cracking, catalytic naphtha cracking and the conversion of methanol to olefins (MTO). However, in addition to linear butenes, the C4 olefinic streams resulting from these processes typically contain significant quantities of butadiene isobutylene and saturated C4 hydrocarbons (n-butane and iso-butane). Accordingly, before they can be used in processes such as the production of LLDPE, these olefinic streams must be treated to reduce the butadiene and isobutylene impurities to acceptable levels.

Separation of butadiene or isobutylene from 1-butene by fractionation is difficult due to the close boiling points of the two impurities to 1-butene. Such fractionation processes therefore require large distillation towers and can be prohibitively expensive. A practiced option is extractive distillation with a selective solvent. However, although butadiene can be effectively removed from C4 olefins by this technique, similar technology is unavailable for removal of isobutylene. Moreover, butadiene extractive distillation requires additional equipment for solvent separation and recovery.

Selective hydrogenation processes are capable of removing butadiene from C4 olefinic streams by conversion of the butadiene to butenes, butane, or dimerized (C8) or trimerized (C12) products. Thus, for example, U.S. Pat. No. 5,227,553 discloses a process for the selective hydrogenation of butadiene to butenes in the liquid phase or trickle phase in contact with a fixed-bed of supported noble metal catalyst, wherein a C4 stream having a butadiene content of from 20 to 80% by weight is hydrogenated in a cascade of two reaction zones such that the hydrogenation product from the first reaction zone has a butadiene content of from 0.1 to 20% by weight and the hydrogenation product from the second reaction zone has a butadiene content of from 0.005 to 1% by weight.

In addition, U.S. Pat. No. 6,169,218 discloses a process for the removal of diolefins and acetylenic compounds in an olefin rich aliphatic hydrocarbon stream by selective hydrogenation at a temperature 40 to 300° F. and low hydrogen partial pressure in the range of about 0.1 psia to less than 70 psia in a distillation column reactor.

However, although selective hydrogenation processes are effective in removing butadiene without significant loss of linear butenes in the feed, they cannot remove isobutylene in a similar manner. Thus the order of hydrogenation activity of the olefinic C4 species is as follows: butadiene >1-C4=>iC4=. Thus, isobutylene cannot be hydrogenated without first hydrogenating the desired 1-butene.

One known process for separating isobutylene from linear butenes is via the production of methyl tert-butyl ether (MTBE). In this process, methanol is reacted selectively with isobutylene in a C4 olefinic stream using an acidic catalyst to produce MTBE with little loss of linear butene product. Although effective, this method of separation has some disadvantages. Thus, butadiene cannot be removed under the same conditions and the formation of MTBE is not 100% selective so that additional oxygenates are also produced. Moreover, extensive recovery equipment is needed to remove the oxygenates and recover any unreacted methanol from the product stream. In addition, there is the potential for future restrictions on the use of MTBE, which could make the production of MTBE unattractive.

There is therefore a need for a process which is effective to selectively remove both isobutylene and butadiene from C4 olefinic streams without the need for extensive recovery equipment.

U.S. Pat. No. 4,454,367 discloses a process for removing isobutene in 1-butene without loss of the 1-butene by selectively oligomerizing the isobutene over a high silica mordenite catalyst.

U.S. Pat. No. 5,955,640 discloses an integrated process for the production of butene-1 from a C4 hydrocarbon stream in which the hydrocarbon stream is initially fed to a selective hydrogenation section to remove butadiene and acetylenic compounds. The hydrogenated stream is then fed to a distillation section to separate a butene-1 product fraction and then to a molecular sieve separation section to remove butenes. The remaining hydrocarbon stream (composed of butene-1 and butenes-2) is then fed to a double bond isomerization section to convert the cis and trans butenes-2 to butene-1, whereafter the isomerization effluent is mixed with fresh feed and recycled back to the selective hydrogenation section.

U.S. Pat. No. 6,215,036 discloses a process for producing isobutene from a C4 olefinic hydrocarbon cut containing isobutene as well as but-1-ene and but-2-enes. The process comprises passing the hydrocarbon cut into a distillation zone associated with a hydroisomerization reaction zone, wherein the hydroisomerization zone is at least partly external to the distillation zone. The hydroisomerization zone selectively converts the but-1-ene into but-2-enes, which can be separated from the isobutene in the distillation zone.

International Patent Publication Number 01/46095 discloses a process for producing trimethylpentenes by selectively dimerizing isobutene in a C4 olefinic feedstock containing isobutene and n-butenes over a zeolite beta catalyst.

U.S. Patent Application Publication No. 2002/0002316 discloses a process for the production of high octane number hydrocarbons by the selective dimerization of isobutene in a hydrocarbon cut having a linear olefin/isobutene ratio >3 over an acid catalyst, such as phosphoric acid, cationic exchange acid resins, liquid acids such as H2SO4, sulfonic acid derivatives, silica-aluminas, mixed oxides, zeolites, and fluorinated and chlorinated aluminas.

U.S. Patent Application Publication No. 2002/0128528 discloses a process for selectively removing acetylene compounds from the effluent of a steam cracker comprising passing the effluent into a distillation zone associated with a hydrogenation reaction zone external to the distillation zone. The acetylene compounds are converted to olefins and oligomers in the hydrogenation reaction zone and the oligomers are withdrawn as heavies from the distillation zone.

SUMMARY

According to one aspect of the present invention, there is provided a process for selectively removing isobutene and butadiene from a stream, in particular a C4 olefinic stream, the process comprising contacting the stream with a hydrogenation catalyst to hydrogenate butadiene and an oligomerization catalyst to oligomerize isobutene.

In a further aspect, the invention resides in a process for selectively removing isobutene and butadiene from an olefinic stream further comprising linear butenes, the process comprising:
  (a) contacting the olefinic stream under hydrogenation conditions with a hydrogenation catalyst to selectively hydrogenate butadiene in the olefinic stream, and
  (b) contacting the olefinic stream under oligomerization conditions with an oligomerization catalyst to selectively oligomerize isobutene in the olefinic stream. The stream can then be passed to a recovery section to recover unconverted linear butenes.

Conveniently, the hydrogenation catalyst includes at least one metal selected from Groups 8, 9, 10 and 11 of the Periodic Table of Elements. In one embodiment, the hydrogenation catalyst also includes a porous inorganic oxide support, such as silica, alumina, zirconia, titania, an aluminophosphate, a clay or a crystalline molecular sieve.

Conveniently, the oligomerization catalyst includes a solid acid catalyst, such as a crystalline molecular sieve, substituted silicate, structured polyacid, acidified resin, mixed metal oxide or sulfated zirconia.

It is to be appreciated that references to the Periodic Table of Elements in the present specification are directed to the IUPAC format described in the CRC Handbook of Chemistry and Physics, 78th Edition, CRC Press, Boca Raton, Fla. (1997).

DETAILED DESCRIPTION OF THE EMBODIMENTS

Introduction

Figure 1:
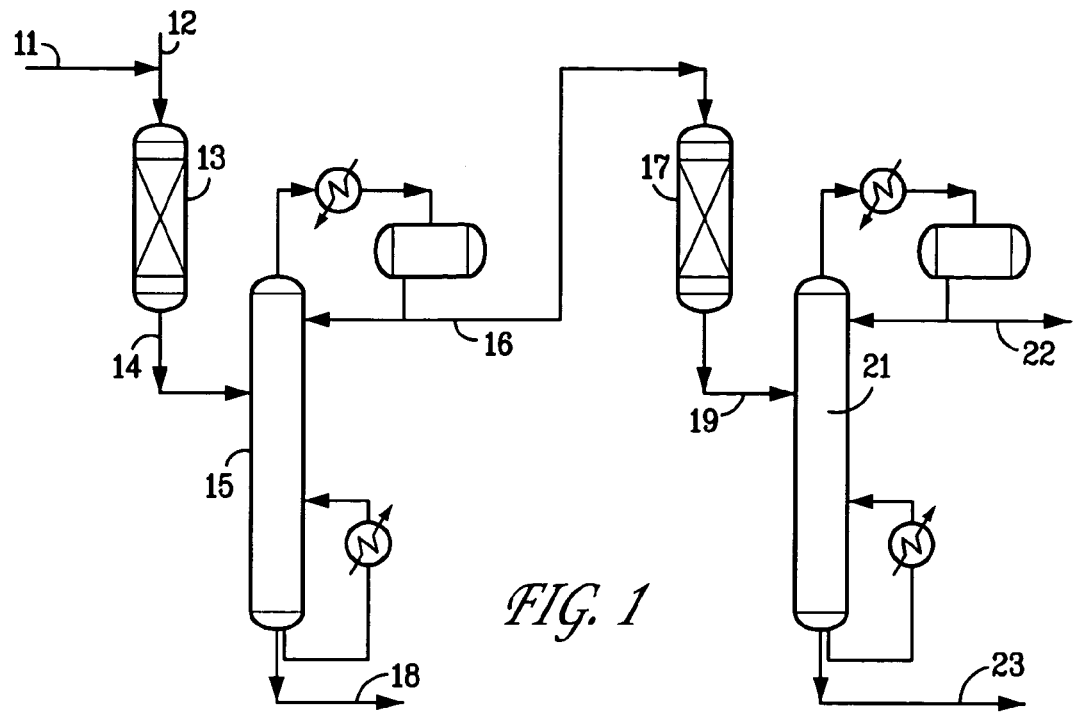
FIG. 1 is a schematic flow diagram of a process according to a first embodiment of the present invention for removing the butadiene and isobutylene impurities from a C4 olefin-containing stream.

The present invention provides a process for removing both butadiene and isobutylene impurities from C4 olefin-containing streams without requiring extensive product recovery. The process includes a selective hydrogenation step for the removal of at least part of the butadiene impurity and a selective oligomerization step for removal of at least part of the isobutylene impurity. The selective hydrogenation step and the selective oligomerization step are operated in series, normally with the hydrogenation step preceding the oligomerization step, and are typically followed by a C4 recovery step.

Feedstock

Potential feed streams for use in the present process include the C4+ components from any olefin producing process, such as steam cracking, fluid catalytic cracking, catalytic naphtha cracking and the conversion of methanol to olefins (MTO). Possible feed stream compositions comprise from about 0.01 to about 80% by weight, such as from about 0.1 to about 40% by weight, of butadiene and from about 0.1 to about 35%, such as from about 1 to about 30% by weight, of isobutylene, with the balance being linear butenes and, optionally, butenes and/or C5+ olefins.

Butadiene Removal Step

The butadiene removal step of the present process involves contacting the feed stream with hydrogen in the presence of a hydrogenation catalyst to selectively hydrogenate butadiene in the stream. The butadiene is thereby converted into one of three products, namely butenes, butenes, or C5+ oligomers (i.e. butene dimers or trimers).

A wide variety of hydrogenation catalysts can be employed in the butadiene removal step, but in general a supported metal catalyst is preferred. Such a catalyst typically includes (1) a first component including one or more metals from Groups 8, 9, 10, 11 of the Periodic Table of Elements, (2) a second component comprising at least one porous inorganic oxide and (3) a third optional component comprising sulfur or oxygen. Non-limiting examples of suitable metal components include nickel, palladium, platinum, rhodium, ruthenium and mixtures thereof. Non-limiting examples of suitable porous inorganic oxides include silica, alumina, zirconia, titania, aluminophosphate, clay and microporous crystalline molecular sieves, such as silicates, aluminosilicates, substituted aluminosilicates, aluminophosphates and substituted aluminophosphates, and mixtures thereof.

The reactions conditions employed in the butadiene removal step typically include a temperature in the range of about 20° C. to about 180° C., such as about 40° C. to about 100° C., a pressure of about 0 psig to about 500 psig (100 to 3550 kpaa), such as about 200 psig to about 400 psig (about 1400 to 2800 kPa), and a H2/BD molar ratio of about 0.5 to about 20, such as about 1 to about 10.0. The butadiene removal step is conveniently effected in the liquid phase with the LHSV typically being in the range of about 0.1 to about 50 hr−1, such as about 1 to about 25 hr−1.

Isobutylene Removal Step

The isobutylene removal step of the present process involves contacting the feed stream with a selective oligomerization catalyst, normally a solid acid catalyst. Due to the higher reactivity of isobutylene compared to linear butenes in acid catalysis, isobutylene can be selectively converted to olefin oligomers (i.e. butene dimers or trimers) with minimal losses of the desired linear butene products.

Solid acid catalysts useful for the selective oligomerization of isobutylene typically include (1) at least one first solid acid component, such as a crystalline molecular sieve, an amorphous aluminosilicate or other substituted silicate, a structured polyacid, an acidified resin and sulfated zirconia, and, optionally, (2) a second binder component of such as clay, silica, alumina or aluminophosphate. The components may be chemically and/or physically mixed.

Molecular sieves suitable for use in the solid acid catalyst include the more common 8-, 10- and 12-member rings zeolites having the AEL, MFI, MEL, MFS, MEI, MTW, EUO, MTT, HELI, FER, TON, FAU, CHA structures. Examples of these zeolites include faujasites (e.g. X and Y zeolites), ZSM-5, ZSM-11, ZSM-12, ZSM-22, ZSM-23, ZSM-34, ZSM-35, ZSM-48, ZSM-50, ZSM-57, mordenite and zeolite beta. In addition, silicophosphoaluminate molecular sieves, (e.g. SAPO-5, SAPO-11, SAPO-14, SAPO-17, SAPO-18, SAPO-20, SAPO-31, SAPO-34, SAPO-41 and SAPO-46) and substituted aluminophosphate molecular sieves (e.g. MeAPO, MeAPSO, ELAPO and ELAPSO) can be used. Molecular sieves with larger channel structures such as VPI-5 and the mesoporous M41S series (e.g. MCM-41) or their substituted equivalents may also be used. The molecular sieves can be used in the protonic form or any other cationic form (e.g. Na+, Ag+, Ca2+, Mg2+, Zn2+, Co2+, Ga2+, Fe3+ and Bi3+).

The reactions conditions employed in the isobutylene removal step are conveniently the same or similar to those used in the butadiene removal step. In particular, the conditions typically include a temperature in the range of about 20° C. to about 180° C., such as about 40° C. to about 100° C., and a pressure of about 0 psig to about 500 psig (100 to 3550 kpaa), such as about 200 psig to about 400 psig (about 1400 to 2800 kPa). The butadiene removal step is conveniently effected in the liquid phase with the LHSV typically being in the range of about 0.1 to about 50 hr−1, such as about 1 to about 25 hr−1.

Process Configuration

The butadiene removal stage is generally positioned upstream of the isobutylene removal stage since the presence of high levels of butadiene in the feed to the isobutylene removal stage can cause rapid deactivation of the solid acid oligomerization catalyst. Thus the conditions should be severe enough in the first stage to hydrogenate the butadiene to acceptably low levels before reaching the second isobutylene oligomerization stage.

Conveniently, both the butadiene removal stage and the isobutylene removal stage are operated in the liquid phase in order to (1) manage heat release from the reaction exotherms and (2) to provide more effective mass transfer of heavy product species to minimize catalyst deactivation. The butadiene removal stage, as in conventional selective hydrogenation processes, is operated within an adiabatic temperature zone. The isobutylene removal stage is operated within a temperature-controlled zone to prevent excessive polymerization of olefins. An example of a possible temperature control scheme for the isobutylene removal zone could involve vaporizing steam in a heat exchanger-like arrangement.

The effluent from the impurity removal stages is sent to a C4 recovery section where the C4 product is separated from the oligomers. Since the isobutylene removal stage produces C8+ products similar to the butadiene removal stage, the C4 recovery from the two impurity removal stages can be conducted in a recovery section comparable in design to those used in conventional butadiene converters. Complex recovery schemes like those required in isobutylene removal via MTBE production can thereby be avoided.

Optionally, the C4 product stream can be further fractionated to recover butenes. Desired butene products can be recovered in number of ways. When 1-butene is a desired product, the recovery section can be operated to separate 1-butene from 2-butene. When it is not necessary to separate 1-butene from 2-butene for downstream applications, on-spec linear butenes can be produced.

A further advantage of the proposed process is that the impurity removal stages can operate under similar conditions of temperature and pressure, thereby avoiding the need for additional heat exchange equipment or compressors between stages. It follows from this advantage that the two stages can be contained within a single reaction vessel.

Referring now to the drawings, FIG. 1 illustrates a butadiene and isobutylene removal process according to a first embodiment of the invention. In this embodiment, a C4+ olefin stream 11 and hydrogen 12 are first contacted in a butadiene removal reactor 13 and the effluent stream 14 is sent to a first distillation column 15. A stream 16 having a lower butadiene content than the original stream 11, is sent overhead to a second oligomerization reactor 17 to remove isobutylene. C5+ olefins are removed in the bottoms stream 18 of the first column 15. The effluent 19 from the second reactor 17, having a lower isobutylene content than the original stream 11, is sent to a second distillation column 21 to recover C4s as overhead 22. Heavies from the isobutylene removal stage are separated in the bottoms stream 23 of the second column 21.

Figure 2:
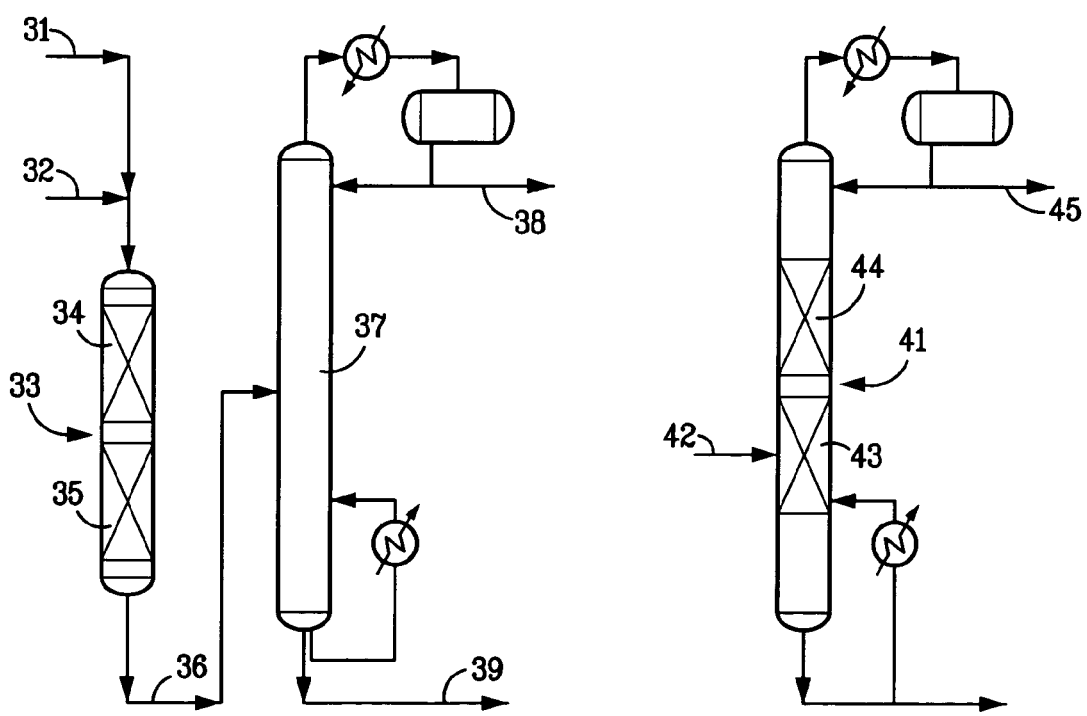
FIG. 2 is a schematic flow diagram of a process according to a second embodiment of the present invention for removing the butadiene and isobutylene impurities from a C4 olefin-containing stream.

A simplified process, employing fewer process vessels, is shown in FIG. 2. In the embodiment of FIG. 2, hydrogen 31 and a C4+ olefin stream 32 are fed to a reactor 33 which contains a bed of hydrogenation catalyst 34 stacked on a bed of oligomerization catalyst 35 such that the catalyst 34 is upstream of the catalyst 35. Effluent 36 from the reactor 33, having a lower content of both butadiene and isobutylene than the stream 32, is sent to a distillation column 37, where C4's are recovered as overhead 38 and C5+ olefins are recovered in the bottoms stream 39.

Figure 3:
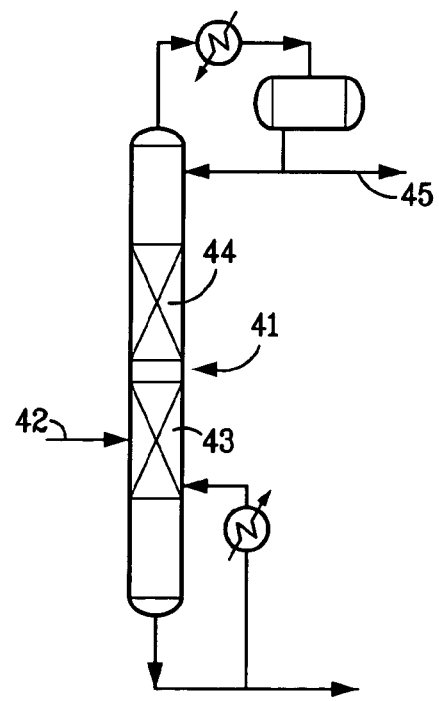
FIG. 3 is a schematic flow diagram of a process according to a third embodiment of the present invention for removing the butadiene and isobutylene impurities from a C4 olefin-containing stream.

A further simplified process, employing a single process vessel, is shown in FIG. 3. In the embodiment of FIG. 3, the butadiene and isobutylene removal stages are contained in a catalytic distillation reactor 41. A feed 42 comprising a C4+ olefin stream and hydrogen is first contacted with the butadiene hydrogenation catalyst 43. C5+ olefins produced in the hydrogenation process are sent to the bottom of the reactor 41, whereas C4's and lighter components are sent upwards to the isobutylene oligomerization catalyst 44. Heavies formed from the isobutylene oligomerization stage are sent to the bottom of the reactor 41 and C4 products are recovered as overhead 45.

The invention will now be more particularly described with reference to the following Example.

EXAMPLE

This example illustrates that both butadiene and isobutylene can be removed from a stream containing C4 olefins in a single reactor utilizing a stacked catalyst bed without significant loss of the desired 1–C4=product.

LD-265 from Procatalyse (0.3 wt % Pd/Al2O3, 2-3 mm beads) and H-Beta (Si/Al=29, 1/16 in. extrudate) from UCI were first calcined at 600° C. in a muffle furnace under air flow for 6 hours. A reactor was charged with the two catalysts in a stacked bed configuration: (1) 5 mL of LD-265, mixed 1:1 by volume with inert mullite beads, and (2) 5 mL of H-beta, also mixed 1:1 by volume with inert mullite beads. The LD265 was placed upstream of the H-beta such that the incoming feed contacted the LD-265 first and the H-beta second. Hydrogen was passed over the catalysts at a flow rate of 275 GHSV (atmospheric pressure) with respect to the LD-265 catalyst. The reactor was then heated to 232° C. and held at this temperature for 16 hours. The reactor was then cooled to 50° C. under nitrogen flow and subsequently pressurized to 240 psig. A feed comprising 2.2 mol %

1,3-BD, 3.8 mol % iC4=, 20 mol % 1–C4=, 35 mol % trans-2–C4=, 25 mol % cis-2–C4=, 6.0 mol % n-C4, 10 mol % iC4, 5.6 mol % C5=, and 1.4 mol % C6= was fed at a rate of 2.5 LHSV with respect to both catalysts. Hydrogen was co-fed at H2/BD molar ratio of 1.1. BD and iC4=conversion were measured with increasing time on stream. The results are included in Table 1.

TABLE 1

|  | Feed | 1.6 hours | 6 hours | 15 hours |
|---|---|---|---|---|
| BD conversion (mol %) |  | 38.79 | 86.96 | 92.45 |
| iC$_4^=$ conversion to C$_8^+$ (mol %) |  | 85.30 | 49.31 | 10.89 |
| 1-C$_4^=$ loss (mol %) |  | 1.01 | −0.52 | 0.84 |
| 1-C$_4^=$ purity | 83.84 | 97.22 | 91.14 | 85.24 |

Table 1 illustrates that BD and iC4=can be simultaneously removed with minimal 1–C4=loss. 1–C4=purity is significantly enhanced compared to the feed. BD and iC4=levels can be further lowered with subsequent process optimization. For example, the application of a more active zeolite with either a higher silica-to-alumina ratio, smaller crystallite size, or both, could be effective in further increasing iC4=conversion.

While the present invention has been described and illustrated by reference to particular embodiments, those of ordinary skill in the art will appreciate that the invention lends itself to variations not necessarily illustrated herein. For this reason, reference should be made solely to the appended claims for purposes of determining the true scope of the present invention.

The invention claimed is:

1. A process for selectively removing isobutene and butadiene from an olefinic stream further comprising linear butenes, the process comprising:
   (a) providing an initial C$_4$ olefin steam produced by steam cracking, fluid catalytic cracking, catalytic naphtha cracking or conversion of methanol to olefins;
   (b) contacting said olefinic stream comprising from about 0.1 wt % to about 35 wt % of isobutene, from about 0.01 wt % to about 80 wt % of butadiene, and linear butenes including 1-butene under hydrogenation conditions with a hydrogenation catalyst to selectively hydrogenate butadiene in the olefinic stream, and thereafter
   (c) contacting the olefinic stream after step (b) under oligomerization conditions with an oligomerization catalyst to selectively oligomerize isobutene in the olefinic stream to butene oligomers which are dimers or trimers; and thereafter
   (d) sending the olefinic stream after step (c) to a C$_4$ recovery section and recovering a linear butene stream enhanced in 1-butene purity compared to said initial C$_4$ olefin stream.

2. The process of claim 1, wherein said hydrogenation catalyst includes at least one metal selected from Groups 8, 9, 10 and 11 of the Periodic Table of Elements.

3. The process of claim 1, wherein said hydrogenation catalyst also includes a porous inorganic oxide support.

4. The process of claim 1, wherein said oligomerization catalyst includes a solid acid catalyst.

5. The process of claim 1, wherein the hydrogenation catalyst is contained in a first catalyst bed and the oligomerization catalyst is contained in a second catalyst bed downstream of the first catalyst bed.

6. The process of claim 1, wherein said hydrogenation conditions include a temperature of from about 20° C. to about 180° C., a pressure of about 0 to about 500 psig (100 to 3550 kPaa), a liquid hourly space velocity of about 0.1 to about 50 hr−1 and a hydrogen to butadiene molar ratio of about 1 to about 10.

7. The process of claim 1, wherein said oligomerization conditions include a temperature of about 20° C. to about 180° C., a pressure of about 0 to about 500 psig (100 to 3550 kPaa) and a liquid hourly space velocity of about 0.1 to about 50 hr−1.

8. The process of claim 4, wherein said solid acid catalyst is a crystalline molecular sieve selected from faujasites, ZSM-5, ZSM-11, ZSM-12, ZSM-22, ZSM-23, ZSM-34, ZSM-35, ZSM-48, ZSM-50, ZSM-57, mordenite and zeolite beta.

9. The process of claim 1, wherein said hydrogenation catalyst includes at least one metal selected from the group consisting of nickel, palladium, platinum, rhodium, ruthenium and mixtures thereof.

10. The process of claim 1, wherein said hydrogenation catalyst also includes a porous inorganic oxide support selected from the group consisting of silica, alumina, zirconia, titania, an aluminophosphate, a clay and a crystalline molecular sieve.

11. The process of claim 1, wherein said oligomerization catalyst includes a solid acid catalyst selected from the group consisting of crystalline molecular sieves, substituted silicates, structured polyacids, acidified resins, mixed metal oxides and sulfated zirconia.

12. The process of claim 5, wherein said first catalyst bed and said second catalyst bed are contained in a single reactor.

* * * * *